US008628235B2

(12) United States Patent
Davies

(10) Patent No.: US 8,628,235 B2
(45) Date of Patent: Jan. 14, 2014

(54) THERMAL TEST APPARATUS AND METHOD

(75) Inventor: Peter Davies, Bristol (GB)

(73) Assignee: Airbus Operations Limited, Bristol (GB)

( * ) Notice: Subject to any disclaimer, the term of this patent is extended or adjusted under 35 U.S.C. 154(b) by 430 days.

(21) Appl. No.: 12/926,150

(22) Filed: Oct. 28, 2010

(65) Prior Publication Data

US 2011/0116528 A1 May 19, 2011

(30) Foreign Application Priority Data

Nov. 13, 2009 (GB) .................................. 0919832.6

(51) Int. Cl.
*G01N 25/00* (2006.01)
*G01N 3/02* (2006.01)
*G01K 1/12* (2006.01)

(52) U.S. Cl.
USPC .................. 374/5; 374/109; 374/46; 374/57; 702/33

(58) Field of Classification Search
USPC ............. 374/4, 5, 10–12, 45–53, 55–57, 141, 374/208, 152; 702/33–35
See application file for complete search history.

(56) References Cited

U.S. PATENT DOCUMENTS

| | | | | |
|---|---|---|---|---|
| 2,523,322 | A * | 9/1950 | Ornstein et al. | 374/57 |
| 2,659,462 | A * | 11/1953 | Schwartz et al. | 52/200 |
| 3,789,662 | A * | 2/1974 | Zettler et al. | 374/31 |
| 4,336,708 | A | 6/1982 | Hobgood et al. | |
| 4,500,252 | A * | 2/1985 | Monhardt et al. | 415/9 |
| 4,575,257 | A * | 3/1986 | Ogura et al. | 374/45 |
| H229 | H * | 3/1987 | Phillips | 165/96 |
| 4,812,052 | A * | 3/1989 | Adam et al. | 374/50 |
| 4,854,726 | A * | 8/1989 | Lesley et al. | 374/45 |
| 5,114,098 | A * | 5/1992 | Campbell | 244/121 |
| 5,188,456 | A * | 2/1993 | Burke et al. | 374/50 |
| 5,277,959 | A * | 1/1994 | Kourtides et al. | 428/116 |
| 5,613,776 | A * | 3/1997 | Turner et al. | 374/57 |
| 5,984,524 | A * | 11/1999 | Teshirogi et al. | 374/55 |
| 6,146,412 | A * | 11/2000 | Van Duren | 607/107 |
| 7,070,323 | B2 * | 7/2006 | Wanek et al. | 374/45 |
| 7,083,327 | B1 * | 8/2006 | Shepard | 374/46 |
| 7,866,101 | B2 * | 1/2011 | Boggs, Jr. | 52/202 |
| 7,930,112 | B2 * | 4/2011 | Mattes | 702/36 |
| 8,162,542 | B2 * | 4/2012 | Harman et al. | 374/208 |
| 8,408,020 | B2 * | 4/2013 | Cole et al. | 62/259.2 |
| 2006/0277830 | A1 * | 12/2006 | Boggs | 52/2.22 |

FOREIGN PATENT DOCUMENTS

| | | |
|---|---|---|
| DE | 296 21 935 | 3/1997 |
| EP | 0 792 450 | 9/1997 |
| EP | 1 760 447 | 3/2007 |
| GB | 2331972 A * | 6/1999 |
| JP | 03077046 A * | 4/1991 |
| KR | 2008057752 A * | 6/2008 |
| SG | 141220 A1 * | 4/2008 |

OTHER PUBLICATIONS

Search Report for GB 0919832.6 dated Feb. 2, 2010.

* cited by examiner

*Primary Examiner* — Gail Verbitsky
(74) *Attorney, Agent, or Firm* — Nixon & Vanderhye P.C.

(57) ABSTRACT

Thermal test apparatus comprising a specimen supported by a fixture, a thermal shroud comprising a flexible insulating fabric forming an enclosure around at least a portion of the specimen, and a temperature controlled air supply connected to an opening formed in the enclosure for delivering a supply of temperature controlled air into the enclosure. Also, a method of conducting a thermal test.

12 Claims, 4 Drawing Sheets

THERMAL TEST APPARATUS AND METHOD

This application claims priority to GB Patent Application No. 0919832.6 filed 13 Nov. 2009, the entire contents of which is hereby incorporated by reference.

FIELD OF THE INVENTION

The present invention relates to apparatus and method for conducting a thermal test on a specimen.

BACKGROUND OF THE INVENTION

As part of a test program for a structure, static and fatigue tests may need to be carried out on the structure at an elevated or lowered temperature. The test specimen may be heated/cooled and subjected to a variety of imposed mechanical load scenarios. This test program may be used, for example, to test the whole or part of an aircraft structure, or any other structure.

In some circumstances, it is not practicable or necessary, to heat/cool the entire test specimen. For example, the size and geometry of the test rig supporting the specimen may hinder the use of some heating/cooling arrangements. Also, the thermal test may only be applicable to certain areas of the test specimen. For example, if the test specimen includes metallic and composite components then the thermal loading due to the thermal coefficients of the different materials may only need to be observed at the interface between these two materials.

Therefore, it can be appropriate to isolate a section of the test specimen to be subjected to the thermal test. A thermal shroud (enclosure) may be used for this purpose. Previously, these thermal shrouds have been constructed from wood, or metal, and insulating foam, which makes them heavy and difficult to install. Hot (or cold) air is blown in a closed loop through the shroud such that the specimen achieves a desired, constant temperature. The weight and rigid nature of the shroud can interfere with the mechanical load test. Also, if the geometry of the specimen or supporting rig changes, then extensive modifications may be required to make the shroud fit. Larger thermal shrouds of similar construction can be used to isolate an entire test specimen from ambient by forming an enclosure around the entire specimen.

There is a need for an improved thermal shroud for use in a thermal test of a specimen which overcomes at least some of the above problems.

SUMMARY OF THE INVENTION

A first aspect of the invention provides a thermal test apparatus comprising a specimen supported by a fixture, a thermal shroud comprising a flexible insulating fabric forming an enclosure around at least a portion of the specimen, and a temperature controlled air supply connected to an opening formed in the enclosure for delivering a supply of temperature controlled air into the enclosure.

A further aspect of the invention provides a method of conducting a thermal test on a specimen, comprising supporting a specimen, providing a thermal shroud comprising a flexible insulating fabric forming an enclosure around at least a portion of the specimen, delivering a supply of temperature controlled air into the enclosure via an opening formed in the enclosure, and conducting a thermal test on the specimen.

The invention is advantageous in that the flexible fabric of the thermal shroud enables the shroud to be more easily manipulated for positioning around the specimen and during the test. The shroud also has a lower mass than prior art rigid shrouds, and so places less force on the test specimen. Changes in the specimen, or the test rig in which it is supported, are more easily accommodated by the flexible shroud, whilst the insulating material ensures good thermal properties and lower energy requirements.

Preferably, the shroud forms a sealed enclosure. The use of the word "sealed" in this context is intended to mean substantially airtight but it will be apparent that some leakage of air from within the enclosure will occur as it is not possible to provide a completely airtight arrangement. What is important is that leakage of air is reduced to a minimum to preserve thermal efficiency.

The shroud may have an opening connected to a return path for returning air to the temperature controlled air supply so as to form a closed loop. The air may be supplied to and exhausted from the enclosure by suitable air hoses, or the like. Preferably, the "inlet" and "outlet" openings are provided on opposite sides of the enclosure. A plurality of similar closed loop air supply systems may be provided for introducing temperature controlled air into the enclosure.

The apparatus may further comprise a load frame connected to the specimen for applying mechanical load to the specimen. The load may be applied to the specimen whilst the temperature controlled air is being delivered into the enclosure, such that a combined mechanical load and thermal test can be carried out on the specimen. The flexible shroud is beneficial as deflections in the specimen under load will not be hindered by the shroud and so the accuracy of the test results will be improved.

The shroud may have at least one opening for permitting the specimen, the fixture, the load frame, or cabling to penetrate the shroud. The cabling may be used to connect between sensors on the specimen and recording apparatus of the test rig. Since some of these sensors may need to be inside the enclosure, the cabling may need to penetrate the shroud. Similarly, parts of the fixture, the load frame and other parts of the test rig which may need to be connected to the specimen within the enclosure may need to penetrate the shroud.

Preferably, the or each opening formed in the shroud is sealed. These openings may be the air inlet opening, the air outlet opening, or any other openings for permitting parts of the specimen or test rig to penetrate the shroud. The sealed opening(s) may include a flap. The sealed opening(s) may include a drawstring. Furthermore, the sealed opening(s) may include a hook-and-eye fastening strip.

In a preferred example, the sealed opening has an outer flap with a hook-and-eye fastening strip, an inner flap, and a drawstring in a fabric fold around the opening. The inner flap may seal against whatever article is penetrating the shroud, the opposing sides of the hook-and-eye fastening strip may be attached to the penetrating article and the shroud respectively, and the drawstring can be drawn tight to apply substantially uniform sealing pressure around the opening. The fastening strip helps prevent movement of the shroud relative to the penetrating article. Other fastening means such as a zip, for example, may be used, optionally with a flap type seal, to seal the openings. The drawstring may be a tension strap, ratchet strap, webbing strap, or the like, and may be used alone to seal the openings by gathering the shroud material around the opening.

The shroud may comprise a plurality of fabric sections joined together to form the enclosure. In a preferred embodiment, there are two sections which may form upper and lower "halves" of the enclosure, although they need not be of substantially similar size. Forming the shroud in multiple sections improves ease of fitting the shroud around the specimen.

The shroud may form a "box-like" enclosure with local modifications to accommodate the openings. The openings are preferably circular, or elliptical apertures. Load may be effectively spread from the openings to the "box" shape by providing at least some of the openings as (frusto)conical projections. Cylindrical projections (or "socks") may additionally, or alternatively be provided to form the openings. Cylindrical and conical projections are relatively straightforward to manufacture and make installation of the shroud around the specimen easier. The projections may be of the same material as the remainder of the shroud, and hence may also be insulated.

In the event that the specimen has any sharp edges, which may be difficult for the shroud to seal against, one or more "plugs" having a curved outer edge may be attached to the specimen such that the opening(s) in the shroud can more easily seal against the plugs. A ratchet strap, or the like, may be used to apply a substantially constant sealing tension in the shroud opening against the plug.

The joint(s) between the fabric sections of the shroud are preferably sealed. The sealed joint may include a hook-and-eye fastening strip with the opposing sides of the strip being attached to their respective fabric sections on either side of the joint. The effectiveness of the seal may be improved by providing a flap seal over the interior side of the fastening strip. Alternatively, other fastening means such as a zip, for example, may be used with a flap type seal to seal the joint(s).

The shroud fabric may include a ply of insulating material sandwiched between inner and outer plies. The shroud fabric therefore preferably includes three plies, but may alternatively be constructed of more than three plies. The inner and outer plies may include a polyurethane coated material, for example, for strength. Preferably, the inner ply includes a polyurethane coated polyamide textile. The plies may be stitched together.

Preferably, the shroud is at least partially supported independently of the specimen. For example, tape loops may be provided around the shroud, such that the shroud may be secured to a supporting structure. This can be used to alleviate the weight of the shroud on the specimen, thereby reducing or negating the effect of the weight of the shroud on the specimen under test. Straps, bungees etc. may be used to secure the shroud to the supporting structure, which may be the test rig itself.

The apparatus may further comprise a second temperature controlled air supply for delivering a supply of temperature controlled air inside the specimen. By introducing temperature controlled air also inside the specimen (where possible), it becomes possible to substantially match the temperatures inside and outside the specimen. This can reduce thermal gradients in the specimen and improve the specimen test.

The specimen may be an aircraft, or part thereof. In one embodiment of this invention, the specimen is part of an aircraft lateral wing box, and the shroud is used to control the temperature of a section of the wing box under thermal test. However, the specimen may be the whole, or part, of an aircraft structure or virtually any other structure requiring a thermal test.

The temperature of the specimen within the enclosure is preferably in the range −50° C. to +130° C. However, the temperature range is essentially only limited by the scope of the thermal test and the shroud materials. For elevated temperatures, one or more fan heaters may be used to supply the temperature controlled air into the enclosure. Suitable refrigerating devices may be used for lowering the temperature in the enclosure.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
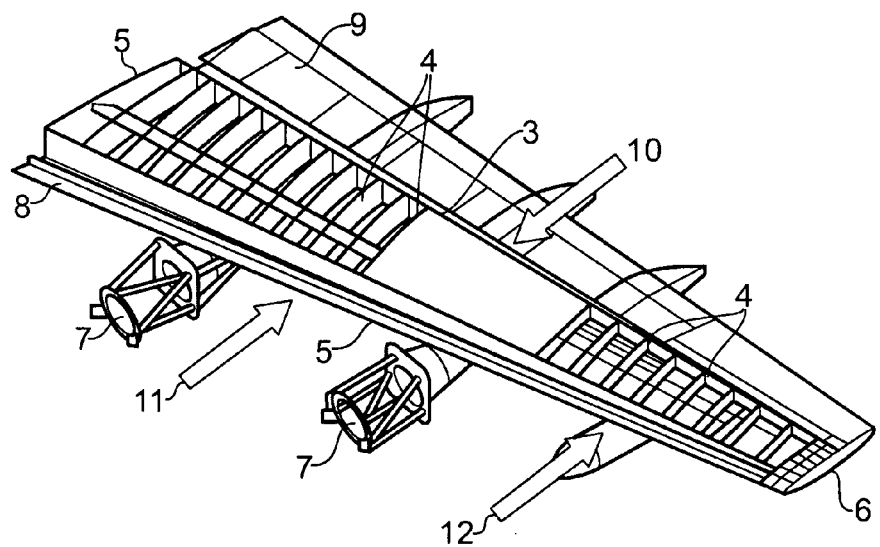
FIG. 1 illustrates an aircraft wing showing the area of interest for thermal testing.

FIG. 1 illustrates an aircraft wing 1 for a medium/large transport jet aircraft, which includes a front spar 2, a rear spar 3, a plurality of chord-wise ribs 4, and upper and lower wing covers 5, 6 to form a typical wing box construction. Engine pylons 7 are slung beneath the wing. Leading edge structures 8 and trailing edge structures 9 are also shown in FIG. 1. The solid arrow indicates an area of interest 10 for conducting mechanical static and fatigue load tests combined with a thermal test on the wing 1.

Due to the size of the wing 1 it is not practicable to conduct the test on the entire wing, and so a test specimen comprising part of the wing box for the wing 1 will be used, which includes the area of interest 10. Arrow 11 indicates a grounding and diffusion area where the test specimen wing box will be mounted and loads in the wing box diffused into the mounting fixture. Arrow 12 indicates a load introduction area where loads will be introduced into the test specimen wing box.

Figure 2:
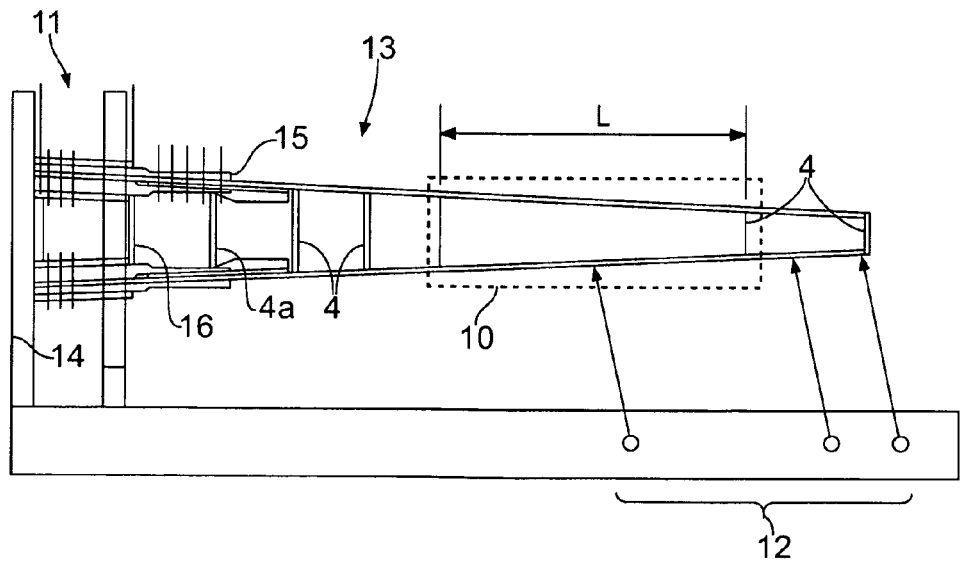
FIG. 2 illustrates a section side view of a partial wing box test specimen for the wing of FIG. 1, and which shows the thermal test area.

FIG. 2 illustrates a test specimen which includes part of the wing box 13 of the wing 1 mounted to a fixture 14. The area of interest 10, the grounding and diffusion area 11, and the load introduction area 12 are indicated also in FIG. 2. The partial wing box 13 is attached to the fixture 14 by metallic plates 15 which are bonded and fastened between the fixture 14 and the partial wing box 13. The rib 4a indicates the last rib of the partial wing box 13 and rib 16 forms part of the fixture 14. Stringer continuity between the partial wing box 13 and the fixture 14 is retained in the grounding and diffusion area 11.

Due to the size and geometry of the partial wing box 13 and the test rig in which it is to be supported for the static and fatigue tests, it is not practicable or necessary to heat the partial wing box 13 in its entirety for the thermal test. The thermal test is therefore restricted to the area of interest 10. In this example, the are of interest 10 occupies a span-wise length, L, of approximately 5 meters and is to be heated to a constant temperature of approximately 70 degrees Celsius for the duration of the tests.

Figure 3:
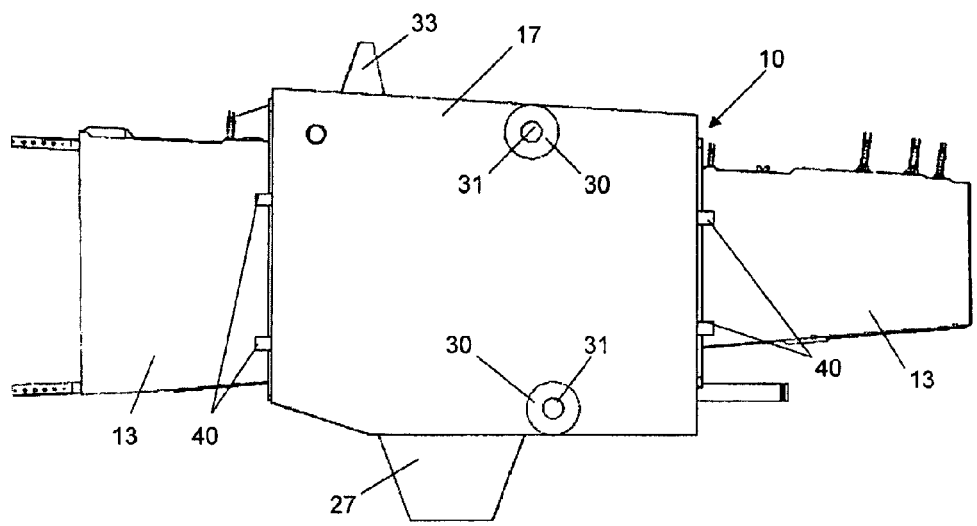
FIG. 3 illustrates a plan view of the partial wing box with a thermal shroud installed.

FIG. 3 illustrates a plan view of a thermal shroud 17 installed around the partial wing box 13 so as to form an enclosure surrounding the area of interest 10.

Figure 4A:
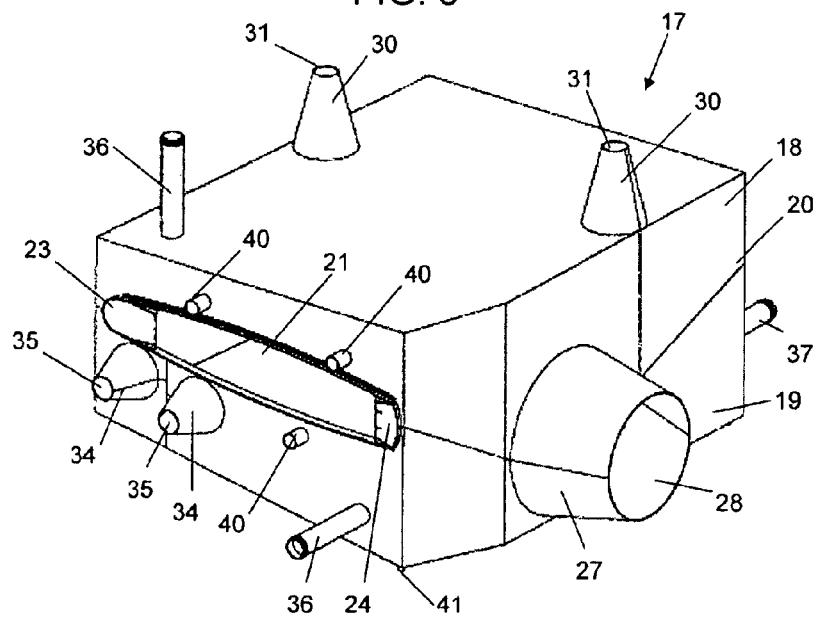
FIGS. 4a and 4b illustrate views of the thermal shroud showing upper and lower sections of the shroud joined together.
Figure 4B:
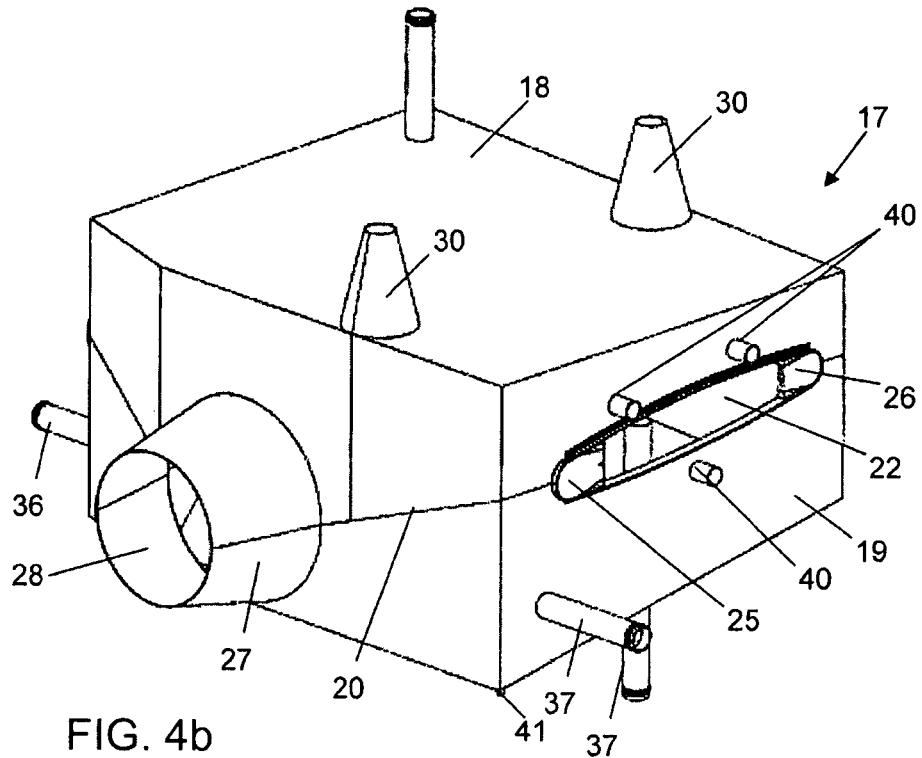

FIGS. 4a and 4b illustrate three-dimensional views of the thermal shroud 17 from different angles. The thermal shroud comprises an upper section 18 and a lower section 19. The upper and lower sections 18, 19 are joined together along joint line 20 which extends around the shroud 17. When joined together, as shown in FIGS. 4a and 4b, the upper and lower sections 18, 19 form a substantially "box like" shape having an array of projections, which will be described in detail below.

The shroud 17 is made of a flexible insulating fabric. The same material is used for the top, bottom, sides and projections of the shroud 17. The shroud material has a three ply construction, comprising an inner ply of polyurethane coated polyamide textile, a mid ply of insulating material and an outer ply of coated polyurethane material. The shroud 17 has a sewn construction from several panels of the material.

The shroud 17 has several openings. The shroud has openings 21 and 22 to permit the partial wing box 13 itself to penetrate the shroud. This is necessary since the shroud 17 does not enclose the entire partial wing box 13. Since the partial wing box 13 has relatively sharp front and rear spar structures 2, 3 (the leading and trailing edge structures 8, 9 do not form part of the test specimen), wooden "plugs" 23-26 are provided, attached to the leading and trailing edges of the partial wing box 13 where the wing box penetrates the shroud 17. In this way, the openings 21 and 22 are void of sharp corners and therefore more easily able to form an effective seal against the partial wing box 13.

A frustro-conical sock 27 extends from the front of the shroud 17 and has a circular opening 28. The sock 27 is adapted to wrap around a dummy engine pylori 29. The dummy pylori 29 simulates the pylori 7. Two further frustro-conical socks 30 extend upwardly from the top of the shroud 17 and having a circular aperture 31. The socks 30 are for wrapping around a load frame 32. A further frustro-conical sock 33 extends rearwardly from the shroud 17 and also has a circular opening. The sock 33 is adapted to wrap around a trailing edge flap gear. Two further frustro-conical socks 34, having circular openings 35, project laterally from beneath the opening 21. The socks 34 are adapted to wrap around a flap track gear (not shown). Two further socks (not shown) extend downwardly from the lower surface of the shroud 17, also having circular openings and adapted to wrap around the flap gear (not shown).

The shroud 17 has several fan inlets and outlets for supplying the enclosure bounded by the shroud 17 with a supply of temperature controlled air. Inlets 36 are provided in the side and top of the shroud 17 at the inboard end, and two outlets 37 are provided in the side and bottom of the shroud 17 and the outboard end. The inlets and outlets are formed as substantially tubular projections and one of the inlets extends inside the shroud 17.

Figure 5:
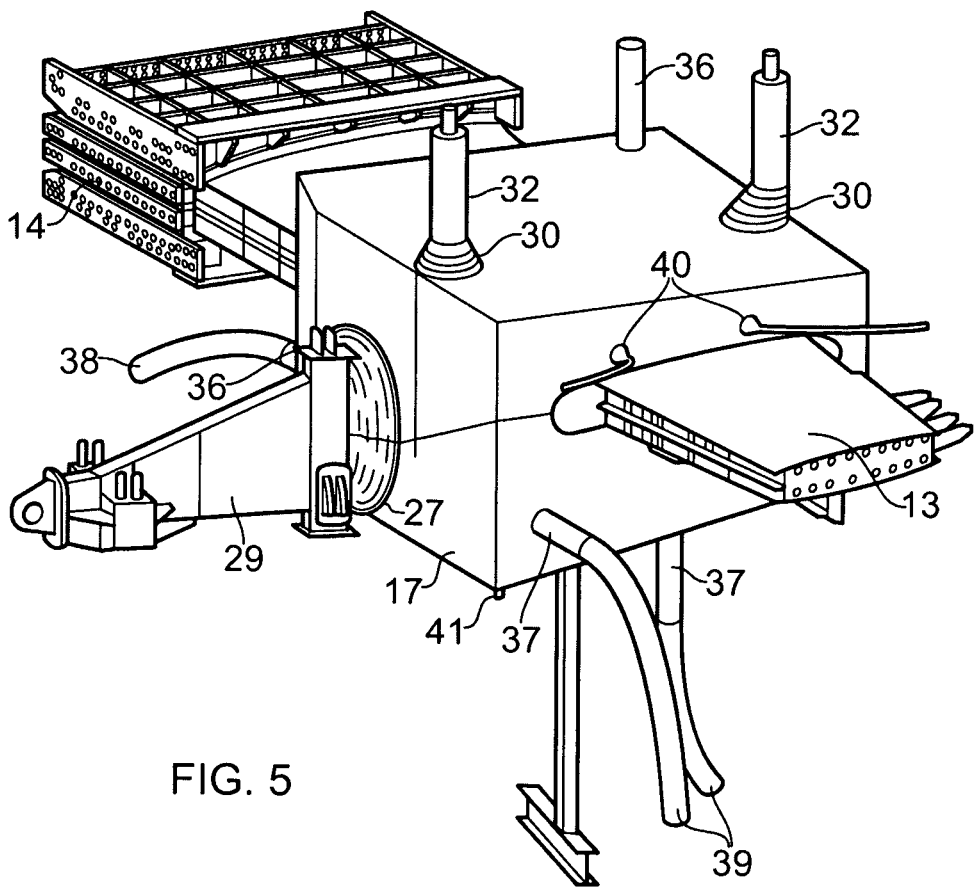
FIG. 5 illustrates the partial wing box mounted in a test rig (some parts removed for clarity) with the thermal shroud installed.

The inlets and outlets are adapted to be connected to fan hoses 38, 39 (shown in FIG. 5). A first pair of the fan hoses 38, 39 form a first closed heated air loop, and a second pair of the fan hoses 38, 39 form a second closed heated air loop. The fan hoses 38 connect between the inlets 36 and respective fan heaters (not shown) of each closed heating loop. The fan heaters may be conventional fan heaters and in this example these are each 40 kW heaters. The return fan hoses 39 connect between the outlets 37 and the fan heater of their respective closed loop. Temperature sensors mounted within the enclosure monitor the temperature of the partial wing box 13 within the enclosure and the sensor output is fed back to the fan heaters for controlling the supply of hot air via the fan hoses 38 to the enclosure. The temperature sensors and fan heaters therefore form part of a closed loop control system of conventional type.

The shroud 17 also has several small cylindrical openings 40 for permitting cabling to pass through the shroud 17 from inside the enclosure. The cabling is used to connect between the myriad of sensors, etc. connected to the partial wing box 13 inside the enclosure. A drain sock 41 is sewn to the bottom surface of the shroud 17 to allow moisture or excessive air to be removed. Finally, a plurality of tape loops (not shown) may be provided on the top and bottom surfaces of the shroud 17 that may be used for attaching straps and/or bungees to the remainder of the test rig, for supporting the weight of the shroud 17. Although the shroud 17 in this example has a weight of only around 50-100 kg, which is significantly lighter than the rigid wood/foam prior art shroud constructions, it is nevertheless desirable to support as much of the weight of the shroud as possible so as to mitigate the effects of the weight of the shroud 17 on the partial wing box specimen 13 during the load test.

The upper and lower sections 18, 19 of the shroud 17 are joined along join line 20, which includes a hook and eye fastening strip (not shown). One side of the strip is mounted to the upper section 18 and the other side of the strip to the lower section 19. As can be seen from FIGS. 4a and 4b, the join line 20 extends around the shroud 17 and is only interrupted by the openings 21 and 22 for the wing box specimen 13 to penetrate the shroud, and also by the large opening 28 for the dummy engine pylon 29 to penetrate the shroud. The hook and eye fastening strip sides are attached to their respective upper or lower shroud sections 18, 19 by stitching. The upper shroud section 18 also has a sealing flap (not shown) formed as a flange extending from the interior side of the shroud 17 adjacent to the join line 20. When air is introduced into the enclosure, the flap seal is urged to seal along the join line 20 behind the hook and eye fastening strip and therefore help to prevent escape of hot air from within the enclosure. By providing the hook and eye fastening strips along the join line 20, it becomes easy to position the upper and lower sections 18, 19 of the shroud 17 around the wing box specimen 13.

FIG. 5 illustrates the shroud 17 installed on the partial wing box test specimen 13. The upper and lower sections 18, 19 of the shroud 17 are positioned around the wing box test specimen 13 and then the upper and lower sections 18, 19 are joined together along the join line 20 using the hook and eye fastening strip. The various conical projections 27, 30, 34 are wrapped around the various parts which need to penetrate the shroud 17. The projections are secured with a webbing strap and a hook and eye fastening strip to effect a seal. In this way, the openings 31, 28 and 35 are sealed around the dummy engine pylori 29, the load frame jacks 32 and the flap gear (not shown). The openings 40 for the sensor cabling are secured by drawstrings around the cabling which passes therethrough, and the drain sock 41 is closed off with a tie cord. The openings 21 and 22 are sealed to the wing box test specimen 13 in the manner described below with reference to FIGS. 6-8.

Figure 6:
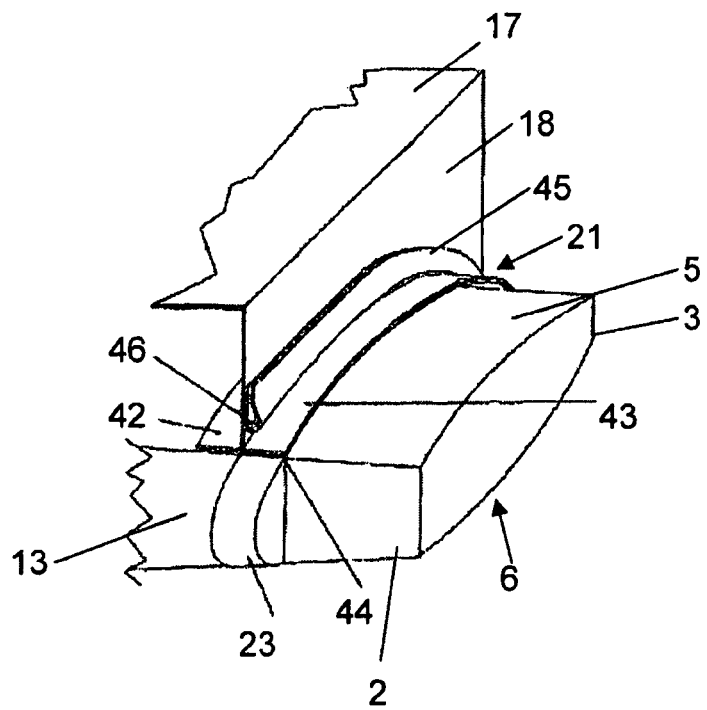
FIG. 6 illustrates a partial cut away view of the upper section of the thermal shroud installed on the partial wing box and showing a sealed opening to permit the wing box to penetrate the shroud.

FIG. 6 illustrates a partial view of the upper shroud section 18 attached to the partial wing box test specimen 13. The wooden plug 23 is fixed to the leading edge 2 of the partial wing box 13. The upper shroud section 18 has an inner seal flap 42 extending inboard of the side wall of the upper shroud section 18. An outer flap 43 extends outboard of the side wall of the upper shroud section 18 and has on its underside one portion of a hook and eye fastening strip 44. The other portion of the hook and eye fastening strip is fixedly attached to the upper cover 5 of the partial wing box test specimen 13.

As the upper shroud section 18 is maneuvered into position around the partial wing box 13, the mating portions of the hook and eye fastening strip 44 are attached to fasten the upper shroud section 18 to the wing box test specimen 13. This helps prevent lateral movement of the shroud 17 relative to the partial wing box 13. Attached to the side wall of the shroud 17 around the opening 21 is a fold 45 which accommodates a drawstring 46. The fold 45 is stitched to the side wall of the shroud 17.

Figure 7:
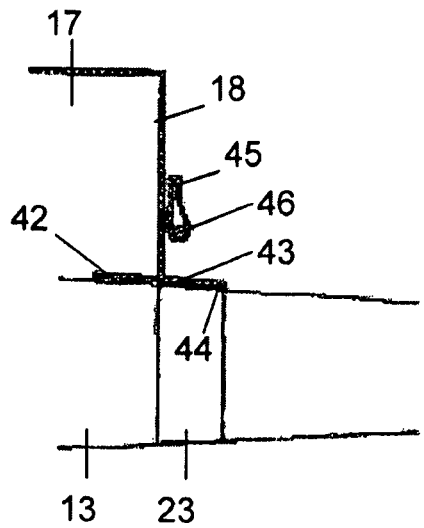
FIG. 7 illustrates a section view of the sealing arrangement shown in FIG. 6 with the drawstring slack.
Figure 8:
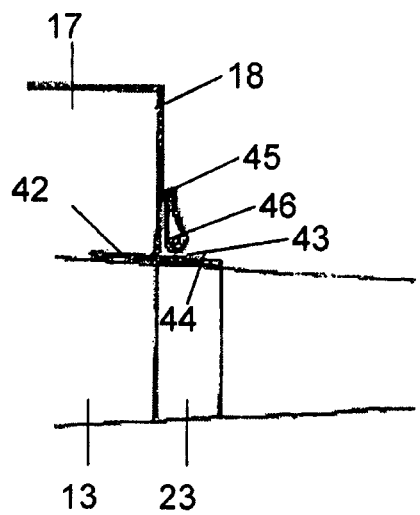
FIG. 8 illustrates a section view of the sealing arrangement shown in FIG. 6 with the drawstring pulled tight.

FIG. 7 illustrates a section view looking aft of the arrangement depicted in FIG. 6 showing the drawstring 46 slack, and FIG. 8 illustrates the arrangement with the drawstring 46 pulled tight. Pulling the drawstring 46 tight around the opening 21 ensures that the two portions of the hook and eye fastening strip 44 do not detach from one another when the hot air is fed inside the shroud 17. The inner flap seal 42 seals against the upper cover 5 of the partial wing box 13 inside the enclosure to form a good sealing engagement when the hot air is fed inside the shroud 17. It will be appreciated that the same sealing arrangement including an inner flap seal, an outer flap having a hook and eye fastening strip, and the fold having the drawstring is continued around the entire periphery of each of the openings 21 and 22 so as to seal between the shroud 17 and the partial wing box test specimen 13 and the plugs 23-26. As explained previously, the plugs 23-26 improve the quality of the seal with the shroud 17 around the openings 21 and 22 as they have a smooth curved outer surface.

Returning to FIG. 5, it can be seen that the shroud 17 is sealed around the area of interest 10 of the wing box test specimen 13 so as to form a substantially airtight enclosure.

Since the shroud 17 is attached by straps and/or bungees to the remainder of the test rig, the shroud 17 assumes a substantially box like shape as shown in FIG. 5. Hot air is then introduced into the enclosure via the inlet tubes 36 so as to fill the enclosure with hot air. The hot air heats the portion of the partial wing box 13 within the enclosure and the air is recirculated via the outlet tubes 37 and the return fan hoses 39 to the fan heaters for reheating and recycling the hot air back via the fan hoses 38 to the inlet tubes 36 until the partial wing box test specimen 13 achieves a desired, predetermined elevated temperature.

Temperature sensors on the partial wing box 13 within the enclosure are used to control the heat output of the fan heaters to maintain the predetermined temperature within the enclosure. Once the predetermined temperature has been reached at a steady state, a mechanical load can be applied to the wing box test specimen using the load frame 32 to conduct a static or fatigue load scenario and the results of this combined thermal and mechanical load test can be monitored and recorded. The load test itself is entirely conventional so will not be described further here.

The predetermined temperature for the wing box test specimen 13 may be approximately 70 degrees Celsius. However, it will be appreciated that the thermal shroud 17 may be used across a wide variety of elevated or lowered temperatures.

Whilst in the example described above, fan heaters are used to elevate the temperature within the enclosure, it will be appreciated that suitable refrigerating fan devices may similarly be used to lower the temperature within the enclosure relative to the ambient temperature. Depending upon the test specimen and the thermal test to be conducted the temperature of the test specimen may be varied typically in the range −50 degrees Celsius to +130 degrees Celsius. However, it will be appreciated that temperatures outside of this range are achievable if desired, and are only limited by the materials of the shroud 17 and the desired thermal test.

As will be appreciated, the partial wing box 13 has a hollow interior construction which may result in thermal gradients within the partial wing box itself. As these thermal gradients are generally undesirable, a further fan heater (not shown) can be used to deliver a supply of temperature controlled air inside the partial wing box 13 in the area of interest 10. By heating both the inside and the outside of the wing box 13, thermal gradients through the test specimen are reduced to a minimum, which improves the accuracy of the test result.

Whilst the above described test is conducted at a stable, predetermined temperature, it will be appreciated that an alternative test scenario may include varying the temperature of the test specimen through a predetermined range. Furthermore, whilst the exemplary test described above is a combined mechanical load and thermal test, it will be appreciated that the thermal test may be conducted without an imposed load. For example, a variable temperature test may be conducted in the absence of a load test imposed through the load frame 32.

Although the invention has been described above with reference to one or more preferred embodiments, it will be appreciated that various changes or modifications may be made without departing from the scope of the invention as defined in the appended claims.

The invention claimed is:

1. Thermal test apparatus for a specimen supported by a fixture, said apparatus comprising:
    a thermal shroud comprising a flexible insulating fabric, said fabric configured to form an enclosure around at least a portion of the specimen, and an interior of said enclosure comprised of space between said specimen and said enclosure; and
    at least one temperature controlled air supply connected to an opening formed in the enclosure for delivering a supply of temperature controlled air into the interior of said enclosure.

2. Apparatus according to claim 1, wherein the shroud forms a sealed enclosure.

3. Apparatus according to claim 1, wherein the shroud has an opening connected to a return path for returning air to the temperature controlled air supply so as to form a closed loop.

4. Apparatus according to claim 1, further comprising a load frame connected to the specimen for applying mechanical load to the specimen.

5. Apparatus according to claim 1, wherein the shroud has at least one opening for permitting the specimen, the fixture, a load frame, or cabling to penetrate the shroud.

6. Apparatus according to claim 1, wherein the opening formed in the shroud is sealed.

7. Apparatus according to claim 1, wherein the shroud comprises a plurality of fabric sections joined together to form the enclosure.

8. Apparatus according to claim 7, wherein the joint(s) between the fabric sections are sealed.

9. Apparatus according to claim 1, wherein the shroud fabric includes a ply of insulating material sandwiched between inner and outer plies.

10. Apparatus according to claim 1, wherein the shroud is at least partially supported independently of the specimen.

11. Apparatus according to claim 1, wherein said at least one temperature controlled air supply comprises at least two temperature controlled air supplies.

12. Apparatus according to claim 1, wherein the specimen is an aircraft, or part thereof.

* * * * *